United States Patent [19]

Barth et al.

[11] Patent Number: 4,517,185

[45] Date of Patent: May 14, 1985

[54] 2-PYRROLIN-3-CARBONITRILE DERIVATIVES, AND PHARMACEUTICAL COMPOSITIONS CONTAINING THEM AND THEIR ANTI-INFLAMMATORY AND ULCER PROTECTIVE ACTIVITY

[75] Inventors: Hubert Barth, Emmendingen; Edgar Fritschi, St. Peter; Volker Ganser, Freiburg; Johannes Hartenstein, Stegen-Wittental; Manfred Herrmann, St. Peter; Gerhard Satzinger, Denzlingen, all of Fed. Rep. of Germany

[73] Assignee: Warner-Lambert Company, Morris Plains, N.J.

[21] Appl. No.: 478,762

[22] Filed: Mar. 25, 1983

[30] Foreign Application Priority Data

Apr. 3, 1982 [DE] Fed. Rep. of Germany ....... 3212591

[51] Int. Cl.³ .................. C07D 401/04; C07D 401/14; A61K 31/44; A61K 31/535
[52] U.S. Cl. .................................... 514/232; 514/252; 514/326; 514/422; 544/131; 544/360; 546/193; 546/281; 514/425
[58] Field of Search ................ 546/281, 193; 544/131, 544/360; 424/263, 267, 250, 248.51

[56] References Cited

U.S. PATENT DOCUMENTS 4,329,343  5/1982  Bernhart et al. ............... 424/248.54

Primary Examiner—Alan L. Rotman
Attorney, Agent, or Firm—Ronald A. Daignault

[57] ABSTRACT

The present invention provides compounds of the general formula I

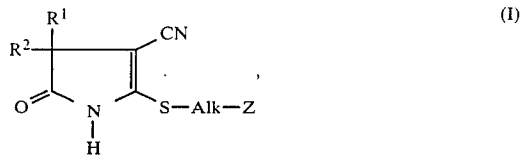

wherein $R^1$ and $R^2$, which are the same or different, are unsubstituted or substituted aromatic rings, Alk is a straight-chained or branched lower hydrocarbon chain and Z is a hydrogen atom, with the proviso that when Alk is a straight-chained hydrocarbon chain, Z can also be a lower alkylamino radical of the general formula II

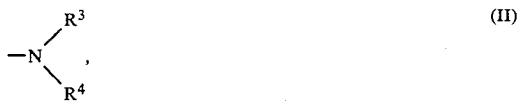

in which $R^3$ and $R^4$ are the same or different and are hydrogen atoms or straight-chained or branched lower alkyl radicals or $R^3$ and $R^4$, together with the nitrogen atom to which they are attached, can also form a ring optionally containing further hetero atoms; and the pharmacologically acceptable salts thereof.

The present invention also provides an inventive process for preparing these compounds, as well as pharmaceutical compositions containing them. The compounds I may be used in the therapy of inflammations and they are free of gastrointestinal side effects.

4 Claims, No Drawings

2-PYRROLIN-3-CARBONITRILE DERIVATIVES, AND PHARMACEUTICAL COMPOSITIONS CONTAINING THEM AND THEIR ANTI-INFLAMMATORY AND ULCER PROTECTIVE ACTIVITY

The present invention is concerned with new 5-oxo-2-pyrroline-3-carbonitriles, with the preparation thereof and with pharmaceutical compositions containing them.

The new 5-oxo-2-pyrroline-3-carbonitriles according to the present invention are compounds of the general formula:

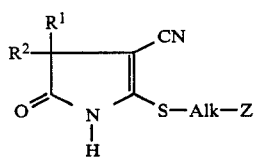

wherein $R^1$ and $R^2$, which can be the same or different, are unsubstituted or substituted aromatic rings, Alk is a straight-chained or branched lower hydrocarbon chain and Z is a hydrogen atom, with the proviso that when Alk is a straight-chained hydrocarbon chain, Z can also be an Amino radical of the general formula:

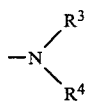

in which $R^3$ and $R^4$ are the same or different and are hydrogen atoms or straight-chained or branched lower alkyl radicals or $R^3$ and $R^4$, together with the nitrogen atom to which they are attached, can also form a ring which optionally contains further heteroatoms; as well as the pharmacologically-acceptable salts thereof.

Compounds of general formula (I) are preferred in which $R^1$ and $R^2$ are the same or different and represent phenyl, pyridyl or thienyl rings which are either unsubstituted or are substituted by up to two halogen atoms, $C_1$-$C_4$ alkoxy radicals, $C_1$-$C_4$ dialkylamino radicals or trifluoromethyl radicals, Alk is a straight-chained or branched $C_1$-$C_4$ alkylene chain and Z is a hydrogen atom, with the proviso that when Alk is a straight-chained alkylene chain, Z can also be an Amino radical of the general formula:

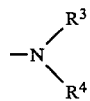

in which $R^3$ and $R^4$ are the same or different and are hydrogen atoms or methyl, ethyl, n-propyl or isopropyl radicals or, together with the nitrogen atom to which they are attached, form a pyrrolidino, piperidino, morpholino or piperazino radical; as well as the pharmacologically acceptable salts thereof.

Especially preferred are compounds of general formula (I) in which $R^1$ and $R^2$ are the same or different and represent phenyl, 4-chlorophenyl, 4-dimethylaminophenyl, 4-fluorophenyl, 4-methoxyphenyl, 2-pyridyl, 3-pyridyl, 2-thienyl or 3-trifluoromethylphenyl radicals and Alk-Z represents a methyl, ethyl, isopropyl, aminoethyl, aminopropyl, ethylaminoethyl, diethylaminoethyl or diethylaminopropyl radical Especially preferred are the compounds of Example 4a (2-(2-diethylaminoethylthio)-4-(4-dimethylaminophenyl)-5-oxo-4-(3-pyridyl)-2-pyrrolin-3-carbonitrile), Example 4i (4-(4-dimethylaminophenyl)-2-methylthio-5-oxo-4-(3-pyridyl)-2-pyrrolin-3-carbonitrile) and Example 4k (2-(3-diethylaminopropylthio)-4-(4-dimethylaminophenyl)-5-oxo-4-(3-pyridyl)-2-pyrrolin-3-carbonitrile).

The present invention also provides a chemically novel process for the preparation of the compounds of general formula (I), wherein a compound of the general formula:

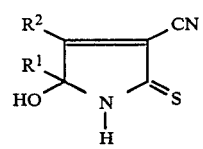

in which $R^1$ and $R^2$ have the same meanings as above, is rearranged in a solvent with a base to give a compound of the general formula:

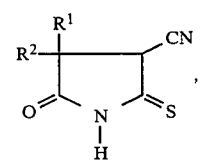

in which $R^1$ and $R^2$ have the same meanings as above, and this subsequently reacted with a compound of the general formula:

in which Z and Alk have the same meanings as above and X is a reactive ester or ether group, and the compound obtained of general formula (I) is subsequently, if desired, converted into a pharmacologically acceptable salt.

In the case of the reaction of a compound of general formula (III) with a base, which is preferably carried out in a polar solvent, for example a low boiling point alcohol, at reflux temperature, a rearrangement takes place with the formation of compounds of general formula (IV).

The solvent used is preferably a polar solvent, especially a lower alcohol, for example methanol, ethanol or n-butanol. The rearrangement reaction requires the presence of a strong base, the preferred bases including potassium hydroxide, potassium carbonate, sodium methanolate, sodium ethanolate and potassium tert.-butylate.

In most cases, the reaction time is from 5 to 30 minutes. The course of the reaction can be monitored by the clearly visible clarification of the initially mostly deep orange to yellow coloured reaction mixture. The rearrangement product can be isolated by careful acidification of the reaction mixture and used as such for the alkylation with a compound of general formula (V).

Preferably, however, the rearrangement product is not isolated but rather reacted directly, in a kind of one-pot reaction, with an appropriate reactive ester or ether of general formula (V). According to the present invention, the reactive ester groups are to be understood to be halogen atoms or alkylsulphate, alkylsulphonate or arylsulphonate radicals. Especially preferred for this purpose are the corresponding halides, sulphates, p-toluenesulphonates and p-bromo-toluenesulphonates. Dialkylaminoalkyl halides are preferably used in the form of their hydrochlorides or hydrobromides. In this case, 2 mole equivalents of base are used for the alkylation reaction. In the case of using a trialkyloxonium salt, X signifies a dialkylether group.

The reaction products of general formula (I) crystallise out directly, after filtering off the precipitated alkali metal halide, from the filtrate or are obtained after concentration of the reaction mixture and partitioning of the residue between a water-immiscible organic solvent, for example methylene chloride, and water, after evaporation of the organic phase and crystallisation of the evaporation residue from an appropriate solvent.

Bases which are difficult to crystallise can be converted into appropriate acid-addition salts. As examples of acid-addition salts, there may be mentioned the salts of organic and inorganic acids, for example, hydrochloric acid, sulphuric acid, phosphoric acid, hydrobromic acid, acetic acid, trifluoroacetic acid, tartaric acid, lactic acid, citric acid, malic acid, salicylic acid, ascorbic acid, malonic acid, maleic acid and succinic acid. The salts are prepared in the usual manner by reacting the bases with appropriate inorganic or organic acids.

The compounds of general formula (III) used as starting materials are obtained by reacting appropriately substituted benzils with 2-cyanothioacetamide in the presence of catalytic amounts of a base, for example triethylamine or piperidine, at ambient temperature or at reflux temperature. The solvent used can be polar and is preferably chloroform, dichloromethane, methanol or ethanol. The reaction time is from 2 to 20 hours.

The mostly yellow or orange coloured compounds of general formula (III) are precipitated during the reaction as hardly soluble precipitates and may be isolated in known manner by filtration, washing and drying once the solvent is removed from the residue.

When using asymmetrical benzils, isomeric products of the general formula (III) can be formed in which $R^1$ and $R^2$ are changed over. However, the subsequent rearrangement and alkylation leads to the same end product of general formula (I). The benzils used are either known or can be prepared by known procedures and methods, for example by oxidation of appropriate benzoins with cupric salts (cf. Organic Reactions, Volume IV, Chapter 5, page 269/1948 and Houben-Weyl, Volume 7/2a, pages 653 and 751).

The compounds of general formula (I) display an activity which represents a new principle in the therapy of inflammatory and ulcerative diseases. Hitherto, inflammation-inhibiting substances of the non-steroidal antiphlogistic type frequently displayed on ulcerogenic side action. In contradistinction thereto, the compounds according to the present invention display an excellent compatibility and a very good inhibition of inflammation, while being surprisingly ulcer-protective.

The compounds of formula (I) may therefore be used in the therapy of inflammation, without gastrointestual side effects exhibited by all known compounds, they are also useful in the therapy of ulcers, due to their ulcer-protective action whis is supported by the antiinflammatory action.

Due to the good compatibility of the compounds and depending upon the degree of severity of the disease to be treated, the dosage in humans is of the order of 50 to 100 mg. in the case of a single dose administered orally or parenterally. Correspondingly, the daily dose amounts to about 100 to 2000 mg.

The compounds of general formula (I) according to the present invention can be administered orally or parenterally in liquid or solid form. As injection solution, it is especially preferred to use water which contains the additives usual in the case of injection solutions, such as stabilising agents, solubilising agents and buffers.

Examples of additives of this kind include tartrate and citrate buffers, ethanol, complex formers (such as ethylenediamine-tetraacetic acid and the nontoxic salts thereof), as well as high molecular weight polymers (such as liquid polyethylene oxide) for viscosity regulation. Examples of solid carrier materials include starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycol); compositions suitable for oral administration can, if desired, additionally contain flavouring and/or sweetening agents.

Consequently, the present invention also provides pharmaceutical compositions containing at least one compound according to the present invention, together with conventional additive and/or carrier materials.

The following experimental report describes the action of the compounds of general formula (I) according to the present invention:

Investigation of the Acute Toxicity

Method

The determination of the acute toxicity was carried out on male mice (NMRI) with a body weight of from 18 to 23 g. All the experimental animals fasted for 20 hours before commencement of the experiment. Water was available ad libitum. Each dosage grouping contained 4 animals. The dosage sequence was logarithmic. The test compounds were administered intragastrally as suspensions in 1% tragacanth slurry. The volume administered was 20 ml./kg. body weight. The animals were observed for a total of 7 days.

Results

The following Table gives the $LD_{50}$ values after a 7 day observation period of the animals:

| Acute toxicity on mice | | |
|---|---|---|
| Compound of Example No. | route of administration | $LD_{50}$ mg/kg. |
| 4a | intragastral | 800 |
| 4b | " | 400 |
| 4d | " | 1600 |
| 4e | " | >1600 |
| 4g | " | 1600 |
| 4i | " | >1600 |
| 4k | " | 300 |
| 6c | " | >1600 |
| 6f | " | >1600 |

Investigation of the Antiphlogistic Action Against Carrageenin Oedema in Rats

Method

The experimental animals used were male rats (SIV 50), fasting for 20 hours, with a body weight of 110 to 160 g. Water was available ad libitum. After determination of the initial value of the paw volume of the right hind leg, the test substance was administered intragastrally as a suspension in 1% tragacanth slurry. 10 animals were used per dosage group. The volume administered was 20 ml./kg. body weight. The paw volume was measured by means of mercury displacement. 60 minutes after intragastral administration of the test substances, 0.1 ml. of a 1% carrageenin solution was injected subplantarily into the right hind paw.

1 and 3 hours after injection of the carrageenin, the paw volume of the oedematous paw was measured. The increase of the paw volume of the test substance-treated animals after 3 hours was compared with that of the control animals and the inhibition of the paw oedema by the test substance was calculated therefrom as a percentage.

Results

The results obtained are summarised in the following Table:

| Antiphlogistic action against carrageenin oedema in rats | | |
|---|---|---|
| Compound of Example No. | dosage mg/kg intragastrally | inhibition of the paw volume in % |
| 4a | 50 | 59 |
|  | 100 | 77 |
| 4d | 50 | 26 |
|  | 125 | 83 |
| 4e | 25 | 37 |
|  | 50 | 70 |
| 4g | 50 | 25 |
|  | 100 | 61 |
| 6c | 125 | 6 |
|  | 250 | 45 |
| 6f | 125 | 24 |
|  | 250 | 45 |

The compounds set out in the above Table show, in the case of a simultaneously good oral compatibility, remarkable antiphlogistic properties, the most effective compounds being those of Examples 4a and 4e.

Investigation of the Influence on Gastric Juice Secretion in Rats

Method

According to the method described by H. Shay et al. (Gastroenterology, 5, 43-61/1945), male rats (SIV 50) with a body weight of 160 to 200 g. were fasted for 48 hours before commencement of the experiment. Water was available to the animals ad libitum. The test substances were administered intragastrally as a suspension in 1% tragacanth slurry. The volume administered was 10 ml./kg. body weight. 8 animals were used per experimental group. One hour after administration of the substance, a pyloric ligature was applied under light ether narcosis. 4 hours after this intervention, the animals were sacrificed. The extirpated stomach was opened up along the curvatura major and the volume of the secretion was measured and compared with the data obtained from the control group.

Results

The following Table summarises the results obtained:

| Influence of gastric juice secretion in rats | | |
|---|---|---|
| Compound of Example No. | dosage in mg/kg intragastral | inhibition of gastric juice secretion in % |
| 4a | 62.5 | 45 |
|  | 125 | 64 |
|  | 250 | 73 |
| 4b | 50 | 24 |
|  | 100 | 63 |
|  | 200 | 76 |
| 4d | 125 | 48 |
|  | 250 | 76 |

As shown by the above Table, for the mentioned test compounds, in the case of Shay's method applied to rats, there was obtained an outstanding, dosage-dependent inhibition of the gastric juice secretion.

Investigation of the ulcer-protective action on gastric ulcers in rats induced by indomethacin

Method

The experimental animals used were male rats (SIV 50), fasted for 20 hours, with a body weight of 170 to 220 g. Water was available ad libitum. The animals were simultaneously given intragastrally 40 mg./kg. indomethacin and the test substance in the form of a suspension in 0.8% "Methocel". The control animals only received the corresponding dosage of indomethacin. 10 animals were used for each experimental group. The volume administered was 10 ml./kg. body weight. 5 hours after administration, the animals were sacrificed. After removal of the stomach and opening along the curvatura major, this was investigated with a stereomagnifier for the presence of ulcers. The ulcers were assessed according to the point scheme suggested by M. Chaumontet et al. (Arzneim. Forsch., 28, 2119/1978) and the ulcer index was calculated therefrom. The ulcer index of the animals treated with indomethacin and test substance was compared with that of the control animals which had only been treated with indomethacin and the ulcer inhibition calculated therefrom as a percentage.

Results

The results obtained are summarised in the following Table:

| Ulcer-protective action of stomach ulcers in rats induced by indomethacin | | |
|---|---|---|
| Compound of Example No. | dosage in mg/kg intragastral | ulcer inhibition in % |
| 4a | 125 | 84 |
| 4i | 50 | 88 |
| 4K | 50 | 33 |
|  | 100 | 94 |

The compounds referred to in the above Table display remarkable ulcer-protective properties, the compound of Example 4i giving an especially favourable therapeutic quotient on the basis of its good compatibility.

The following Examples are given for the purpose of illustrating the present invention:

EXAMPLE 1

2-(2-Diethylaminoethylthio)-4,4-diphenyl-5-oxo-2-pyrroline-3-carbonitrile 10.2 g. 5-Hydroxy-4,5-diphenyl-2-thioxo-3-pyrroline-3-carbonitrile and 9.7 g. anhydrous potassium carbonate are heated under reflux for 20 minutes in 250 ml. ethanol. A solution of 6.0 g. 2-diethylaminoethyl chloride in 50 ml. ethanol is then added dropwise thereto within the course of 10 minutes and boiling continued for 1 hour. The reaction mixture is poured on to ice and the precipitate obtained is filtered off and recrystallised from ethyl acetate. There are obtained 11.9 g. (87% of theory) 2-(2-diethylaminoethylthio)-4,4-diphenyl-5-oxo-2-pyrroline-3-carbonitrile in the form of colourless crystals; m.p. 156°–157° C.

The 5-hydroxy-4,5-diphenyl-2-thioxo-3-pyrroline-3-carbonitrile used as starting material is prepared in the following manner:

A mixture of 60.0 g. benzil, 28.6 g. cyanothioacetamide, 500 ml. methanol and 20 drops of piperidine is stirred at ambient temperature for 5 hours. Thereafter, the solvent is stripped off on a rotary evaporator and the residue obtained is recrystallised from toluene. After drying in a vacuum at 0.1 mm.Hg and 80° C., the desired compound is obtained in the form of yellow crystals; m.p. 195° C. (decomp.).

The following compounds are obtained in an analogous manner:

4,4-diphenyl-5-oxo-2-(2-piperidinoethylthio)-2-pyrroline-3-carbonitrile; m.p. 177°–178° C.;

2-(2-dimethylaminopropylthio)-4,4-diphenyl-5-oxo-2-pyrroline-3-carbonitrile; m.p. 250° C. (decomp.);

4,4-diphenyl-2-ethylthio-5-oxo-2-pyrroline-3-carbonitrile; m.p. 180° C.;

4,4-diphenyl-2-(2-morpholinoethylthio)-5-oxo-2-pyrroline-3-carbonitrile; m.p. 170° C.

EXAMPLE 2

4-(4-Chlorophenyl)-4-(4-dimethylaminophenyl)-2-ethylthio-5-oxo-2-pyrroline-3-carbonitrile 25.9 g. 4-(4-Chlorophenyl)-5-(4-dimethylaminophenyl)-5-hydroxy-2-thioxo-3-pyrrolidine-3-carbonitrile and 19.3 g. anhydrous potassium carbonate are heated for 40 minutes in 400 ml. ethanol. A solution of 7.6 g. ethyl bromide in 40 ml. ethanol is then added dropwise thereto in the course of 15 minutes and boiling continued for 1 hour. After concentration of the reaction mixture, the residue is partitioned between methylene chloride and water, the organic phase is separated off, the solvent is removed in a vacuum and the residue is crystallised from ethanol. There are obtained 18 g. of 4-(4-chlorophenyl)-4-(4-dimethylaminophenyl)-2-ethylthio-5-oxo-2-pyrroline-3-carbonitrile in the form of colourless crystals; m.p. 195° C.

The 4-(4-chlorophenyl)-5-(4-dimethylaminophenyl)-5-hydroxy-2-thioxo-3-pyrroline-3-carbonitrile used as starting material is prepared in the following manner:

A suspension of 60.0 g. p-dimethylamino-p′-chlorobenzil, 19.5 g. cyanothioacetamide and 1 ml. piperidine in 1 liter dichloromethane is stirred at ambient temperature for 20 hours. The precipitated product is filtered off with suction, washed with dichloromethane and recrystallised from ethanol. The desired product is obtained in a yield of 61.9 g. in the form of yellow crystals; m.p. 189° C. (decomp.).

The following compounds are obtained in an analogous manner:

4-(4-chlorophenyl)-4-(4-dimethylaminophenyl)-2-(morpholinoethylthio)-5-oxo-2-pyrroline-3-carbonitrile; m.p. 215° C.;

4-(4-chlorophenyl)-4-(4-dimethylaminophenyl)-5-oxo-2-(2-piperidinoethylthio)-2-pyrrolidine-3-carbonitrile; m.p. 235° C. (decomp.);

4-(4-chlorophenyl)-2-(2-diethylaminoethylthio)-4-(4-dimethylaminophenyl)-5-oxo-2-pyrroline-3-carbonitrile; m.p. 196°–198° C.;

4-(4-chlorophenyl)-2-(3-dimethylaminopropylthio)-4-(4-dimethylaminophenyl)-5-oxo-2-pyrroline-3-carbonitrile; m.p. 180° C.;

2-(2-diethylaminoethylthio)-4-(4-dimethylaminophenyl)-5-oxo-4-phenyl-2-pyrroline-3-carbonitrile; m.p. 169° C.;

4-(4-dimethylaminophenylthio)-2-(2-morpholinoethylthio)-5-oxo-4-phenyl-2-pyrrolidine-3-carbonitrile; m.p. 209° C.;

2-(2-dimethylaminoethylthio)-4-(4-dimethylaminophenyl)-5-oxo-4-phenyl-2-pyrroline-3-carbonitrile; m.p. 172° C.;

4-(4-dimethylaminophenyl)-2-(2-piperidinoethylthio)-5-oxo-4-phenyl-2-pyrroline-3-carbonitrile; m.p. 184° C.;

4,4-bis-(4-chlorophenyl)-2-(2-diethylaminoethylthio)-5-oxo-2-pyrroline-3-carbonitrile; m.p. 166° C.;

2-(2-diethylaminoethylthio)-4,4-bis-(4-methoxyphenyl)-5-oxo-2-pyrroline-3-carbonitrile; m.p. 164° C.

The compounds used as starting materials are prepared as follows:

5-Hydroxy-4,5-bis-(4-methoxyphenyl)-2-thioxo-3-pyrroline-3-carbonitrile 16.5 g. 4,4′-Dimethoxybenzil, 6.0 g. cyanothioacetamide and 15 drops of piperidine were boiled for 2 hours in 200 ml. chloroform on a water separator. The yellow precipitate obtained was filtered off with suction, washed with some chloroform and dried at 80° C. and 0.1 mm.Hg for 12 hours. The desired product is obtained in a yield of 17.6 g. in the form of yellow crystals; m.p. 193° C. (decomp.).

4,5-Bis-(4-chlorophenyl)-5-hydroxy-2-thioxo-3-pyrroline-3-carbonitrile

A suspension of 22.3 g. 4,4′-dichlorobenzil, 6.5 g. 2-cyanothioacetamide, 20 drops of piperidine and 200 ml. chloroform is stirred for 20 hours at ambient temperature. The yellow precipitate obtained is filtered off with suction, well washed with chloroform and dried. There are obtained 22.0 g. of the desired compound in the form of yellow crystals; m.p. 213° C. (decomp.).

5-(4-Dimethylaminophenyl)-5-hydroxy-4-phenyl-2-thioxo-3-pyrroline-3-carbonitrile A mixture of 10.1 g. p-dimethylaminobenzil, 3.2 g. cyanothioacetamide, 10 drops of piperidine and 100 ml. ethanol is stirred for 12 hours at ambient temperature. The precipitated product is filtered off with suction, washed with chloroform and recrystallised from ethanol. There are obtained 6.0 g. of the desired product in the form of yellow crystals; m.p. 184°–185° C. (decomp.).

EXAMPLE 3

2-(2-Diethylaminoethylthio)-5-oxo-4-phenyl-4-(3-trifluoromethylphenyl)-2-pyrroline-3-carbonitrile 19.5 g. 3-Trifluoromethylbenzil, 7.0 g. cyanothioacetamide, 0.5 ml. piperidine and 400 ml. chloroform are stirred for 20 hours at ambient temperature. The yellow suspension is concentrated to about 100 ml. and the yellow precipitate obtained is filtered off with suction, washed and dried. There are obtained 24.0 g. of yellow condensation product; m.p. 200° C. (decomp.).

10.8 g. of the yellow condensation product and 8.3 g. potassium carbonate are boiled, while stirring, for 1 hour in 250 ml. ethanol. A solution of 5.2 g. 2-diethylaminoethyl chloride hydrochloride in 50 ml. ethanol is then added dropwise thereto within the course of 10 minutes, boiling is continued for half an hour and the reaction mixture is finally evaporated on a rotary evaporator. The residue is partitioned between methylene chloride and water and the organic phase is dried. After evaporation, there are obtained 17.5 g. of oily base.

12.6 g. of this base are dissolved in 350 ml. diethyl ether and slowly mixed with a solution of 2.5 g. oxalic acid in 50 ml. diethyl ether. The colourless precipitate obtained is filtered off with suction and recrystallised from ethanol. There are obtained 7.6 g. 2-(2-diethylaminoethylthio)-5-oxo-4-phenyl-4-(3-trifluoromethylphenyl)-2-pyrroline-3-carbonitrile in the form of colourless crystals; m.p. 126° C.

2-(2-Diethylaminoethylthio)-4-(4fluorophenyl)-5-oxo-4-phenyl-2-pyrroline-3-carbonitrile is obtained in an analogous manner: 16.0 g. 4-fluorobenzil and 7.0 g. cyanothioacetamide give a yellow condensation product; m.p. 170°-185° C. 10.8 g. of this condensation product give, after crystallisation of the oily base from ethanol, 11.6 g. of the desired product in the form of colourless crystals; m.p. 127° C.

EXAMPLE 4

2-(Diethylaminoethylthio)-4-(4-dimethylaminophenyl)-5-oxo-4-(3-pyridyl)-2-pyrroline-3-carbonitrile (4a)

2.3 g. Sodium are dissolved in 300 ml. ethanol, 16.8 g. 5-(4-dimethylaminophenyl)-5-hydroxy-4-(3-pyridyl)-2-thioxo-2-pyrroline-3-carbonitrile are added thereto and the reaction mixture is boiled for 30 minutes. A solution of 8.6 g. diethylaminoethyl chloride hydrochloride in 50 ml. ethanol is then added dropwise thereto and boiling continued for 1 hour. The reaction mixture is then concentrated and water is added to the oily residue obtained, followed by extraction with methylene chloride. The organic phase is concentrated and the residue crystallised from ethanol, with the addition of some active charcoal. There are obtained 14.6 g. 2-(2-diethylaminoethylthio)-4-(4-dimethylaminophenyl)-5-oxo-4-(3-pyridyl)-2-pyrroline-3-carbonitrile in the form of colourless crystals; m.p. 150° C.

The 5-(4-dimethylaminophenyl)-5-hydroxy-4-(3-pyridyl)-2-thioxo-3-pyrroline-3-carbonitrile used as starting material is prepared in the following manner:

A suspension of 93.5 g. 3-pyridyl-4-dimethylaminophenylglyoxal, 35 g. cyanothioacetamide and 2 ml. piperidine in 1 liter methanol is stirred for 20 hours at ambient temperature. The red precipitate obtained is filtered off with suction, well washed with methanol and recrystallised from ethanol. The desired compound is obtained in the form of red crystals, the yield being 105.6 g.; m.p. 191° C. (decomp.).

The following compounds are obtained in an analogous manner:

4-(4-dimethylaminophenyl)-2-(2-morpholinoethylthio)-5-oxo-4-(3-pyridyl)-2-pyrroline-3-carbonitrile; m.p. 149° C.; (4b)

4-(4-dimethylaminophenyl)-2-(3-dimethylaminopropylthio)-5-oxo-4-(3-pyridyl)-2-pyrroline-3-carbonitrile; m.p. 152° C.; (4c)

4-(4-dimethylaminophenyl)-2-(2-piperidinoethylthio)-5-oxo-4-(3-pyridyl)-2-pyrroline-3-carbonitrile; m.p. 180° C.; (4d)

4-(4-dimethylaminophenyl)-2-(2-pyrrolidinoethylthio)-5-oxo-4-(3-pyridyl)-2-pyrroline-3-carbonitrile; m.p. 196° C.; (4e)

4-(4-dimethylaminophenyl)-5-oxo-2-(diisopropylaminoethylthio)-4-(3-pyridyl)-2-pyrroline-3-carbonitrile; m.p. 157° C.; (4f)

2-(2-dimetylaminoethylthio)-4-(4-dimethylaminophenyl)-5-oxo-4-(3-pyridyl)-2-pyrroline-3-carbonitrile; m.p. 190° C.; (4g)

4-(4-dimethylaminophenyl)-5-oxo-2-propylthio-4-(3-pyridyl)-2-pyrroline-3-carbonitrile; m.p. 193° C.; (4h)

4-(4-dimethylaminophenyl)-2-methylthio-5-oxo-4-(3-pyridyl)-2-pyrroline-3-carbonitrile; m.p. 206° C.; (4i)

4-(4-dimethylaminophenyl)-2-(3-morpholinopropylthio)-5-oxo-4-(3-pyridyl)-2-pyrroline-3-carbonitrile; m.p. 172° C.; (4j)

2-(3-diethylaminopropylthio)-4-(4-dimethylaminophenyl)-5-oxo-4-(3-pyridyl)-2-pyrroline-3-carbonitrile; m.p. 134° C.; (4k)

4-(4-dimethylaminophenyl)-5-oxo-2-(2-piperazinoethylthio)-4-(3-pyridyl)-2-pyrroline-3-carbonitrile; oxalate m.p. 130° C.; (4l)

4-(4-dimethylaminophenyl)-5-oxo-2-(3-piperidinopropylthio)-4-(3-pyridyl)-2-pyrroline-3-carbonitrile; m.p. 168° C. (4m)

2-ethylthio-4-(4-dimethylaminophenyl)-5-oxo-4-(3-pyridyl)-2-pyrrolin-3-carbonitrile; m.p. 213° C.; (4n)

2-(2-aminoethylthio)-4-(4-dimethylaminophenyl-5-oxo-4-(3-pyridyl)-2-pyrrolin-3-carbonitril; m.p. 205°-206° C.; (4o)

2-(3-aminopropylthio)-4-(4-dimethylaminophenyl)-5-oxo-4-(3-pyridyl)-2-pyrrolin-3-carbonitrile; m.p. 205°-208° C. (decomp.) (4p)

EXAMPLE 5

2-(2-Diethylaminoethylthio)-4-(4-fluorophenyl)-5-oxo-4-(3-pyridyl)-2-pyrroline-3-carbonitrile hydrochloride 27.2 g. 4-Fluorophenyl-3-pyridylglyoxal, 10.0 g. cyanothioacetamide, 10 drops of piperidine and 500 ml. chloroform were stirred for 6 hours at ambient temperature. The precipitated yellow product is filtered off with suction, washed with some chloroform and dried at 60° C. There are obtained 28.2 g. of a yellow condensation product; m.p. 170°-172° C. (decomp.).

2.2 g. Sodium are dissolved in 250 ml. absolute ethanol, 15.0 g. of the condensation product of 4-fluorophenyl-3-pyridylglyoxal and cyanothioacetamide are added thereto and the reaction mixture is boiled for 15 minutes. A solution of 8.3 g. diethylaminoethyl chloride hydrochloride in 50 ml. ethanol is now added dropwise thereto in the course of 15 minutes and the reaction mixture thereafter heated under reflux for 4 hours. After cooling, the solvent is stripped off and the residue is partitioned between chloroform and water. The dried chloroform phase is evaporated to dryness, the oily residue obtained is taken up in anhydrous diethyl ether- /ethanol and the solution is saturated with dry hydrogen chloride. A precipitate initially obtained again goes into solution after a short time. The solvent is stripped off and the residue is triturated with diethyl ether. The solidified product is crystallised from isopropanol and finally again crystallised from ethanol with the addition of a few drops of water. There are obtained 5.1 g. 2-(2-diethylaminoethylthio)-4-(4-fluorophenyl)-5-oxo-4-(3-pyridyl)-2-pyrroline-3-carbonitrile hydrochloride in the form of colourless crystals; m.p. 247° C.

The following compounds are obtained in an analogous manner:

2-(2-Diethylaminoethylthio)-4-(4-methoxyphenyl)-5-oxo-4-(3-pyridyl)-2-pyrroline-3-carbonitrile 12.0 g. 4-Methoxyphenyl-3-pyridylglyoxal and 5.0 g. cyanothioacetamide give 15.8 g. of an orange-coloured product; m.p. 200° C. (decomp.). 10.0 g. of condensation product give, after crystallisation from methanol, 7.8 g. of the desired product in the form of colourless crystals; m.p. 133° C.

2-(2-Diethylaminoethylthio)-5-oxo-4-phenyl-4-(3-pyridyl)-2-pyrroline-3-carbonitrile 20.0 g. Phenyl-3-pyridylglyoxal and 9.5 g. cyanothioacetamide give 23.7 g. of a yellow condensation product; m.p. 140° C. (decomp.). 11.7 g. of condensation product give, after crystallisation from ethanol, 10.5 g. of the desired product in the form of colourless crystals; m.p. 133° C.

2-(2-Diethylaminoethylthio)-4-(3,4-dimethoxyphenyl)-5-oxo-4-(3-pyridyl)-2-pyrroline-3-carbonitrile 24.5 g. 3,4-Dimethoxyphenyl-3-pyridylglyoxal and 8.8 g. cyanothioacetamide give 30.0 g. of a yellow condensation product; m.p. 175°–180° C. (decomp.) (crystallised from ethanol). 15.0 g. of condensation product give, after crystallisation from isopropanol, 10.5 g. of the desired product in the form of colourless crystals; m.p. 133°–135° C.

2-(2-Diethylaminoethylthio)-5-oxo-4-(3-pyridyl)-4-(3-trifluoromethylphenyl)-2-pyrroline-3-carbonitrile oxalate 22.9 g. 3-Pyridyl-3-trifluoromethylphenylglyoxal and 7.0 g. cyanothioacetamide give, after a reaction time of 12 hours, 19.3 g. of yellow condensation product; m.p. 216° C. (decomp.). 19.0 g. of condensation product give 14.0 g. of oily base, the oxalate of which is precipitated out from an ethereal solution. Yield 14.2 g. of the desired product in the form of colourless crystals; m.p. 115° C. (decomp.) (recrystallised from ethanol).

EXAMPLE 6

2-(2-Diethylaminoethylthio)-5-oxo-4-phenyl-4-(2-thienyl)-2-pyrroline-3-carbonitrile (6a)

29.5 g. Benz-2-thenyl, 13.4 g. cyanothioacetamide, 0.5 ml. piperidine and 500 ml. methylene chloride are stirred for 20 hours at ambient temperature. The precipitated product is filtered off with suction and crystallised from ethanol. There are obtained 29.6 g. of greenish crystals (m.p. 187°–189° C.).

14.9 g. of this condensation product of benz-2-thenyl and cyanothioacetamide, together with 13.8 g. potassium carbonate, are heated under reflux, while stirring, for 1 hour in 300 ml. ethanol. A solution of 8.6 g. 2-diethylaminoethyl chloride hydrochloride in 100 ml. ethanol is added dropwise thereto within the course of 10 minutes and boiling continued for 45 minutes. The reaction mixture is concentrated, mixed with water and extracted with methylene chloride. The organic phase is evaporated and the residue crystallised from ethanol. There are obtained 15.3 g. 2-(2-diethylaminoethylthio)-5-oxo-4-phenyl-4-(2-thienyl)-2-pyrroline-3-carbonitrile in the form of colourless crystals; m.p. 165° C.

The following compounds are obtained in an analogous manner:

2-(2-ethylthio)-5-oxo-4-phenyl-4-(2-thienyl)-2-pyrroline-3-carbonitrile; m.p. 115° C.; (6b)
2-(2-morpholinoethylthio)-5-oxo-4-phenyl-4-(2-thienyl)-2-pyrroline-3-carbonitrile; m.p. 185°–186° C.; (6c)
2-(2-piperidinoethylthio)-5-oxo-4-phenyl-4-(2-thienyl)-2-pyrroline-3-carbonitrile; m.p. 180° C.; (6d)
2-(3-diethylaminopropylthio)-5-oxo-4-phenyl-4-(2-thienyl)-2-pyrroline-3-carbonitrile; m.p. 151° C.; (6e)
5-oxo-4-phenyl-2-(2-pyrrolidinoethylthio)-4-(2-thienyl)-2-pyrroline-3-carbonitrile. (6f)

EXAMPLE 7

2-(3-Dimethylaminopropylthio)-5-oxo-4,4-bis-(2-pyridyl)-2-pyrroline-3-carbonitrile 10.2 g. 5-Hydroxy-4,5-bis-(2-pyridyl)-2-thioxo-3-pyrroline-3-carbonitrile and 8.4 g. anhydrous potassium carbonate are heated under reflux for 30 minutes in 250 ml. ethanol. A solution of 4.8 g. 3-dimethylaminopropyl chloride hydrochloride in 30 ml. ethanol is added dropwise thereto and boiling continued for 1 hour. The reaction mixture is then evaporated on a rotary evaporator and the residue is mixed with water and extracted with methylene chloride. The organic phase is dried over anhydrous sodium sulphate, the solvent is stripped off and the oily residue is crystallised from ethanol. There is obtained a yield of 63% of theory of 2-(3-dimethylaminopropylthio)-5-oxo-4,4-bis-(2-pyridyl)-2-pyrroline-3-carbonitrile in the form of colourless crystals; m.p. 184°–185° C.

The 5-hydroxy-4,5-bis-(2-pyridyl)-2-thioxo-3-pyrroline-3-carbonitrile used as starting materials is prepared in the following manner:

11.0 g. 2,2'-pyridyl and 5.0 g. cyanothioacetamide are dissolved in 200 ml. absolute ethanol, 5 drops of piperidine are added thereto and the reaction mixture is heated under reflux for half an hour. After cooling to 0° C., the precipitate obtained is filtered off with suction, washed with some ethanol and recrystallised from ethanol. The crystals obtained are dried for 12 hours at 100° C. and 0.1 mm.Hg. Yield 9.8 g; m.p. 188° C. (decomp.).

The following compounds are obtained in an analogous manner:

5-oxo-2-(2-piperidinoethylthio)-4,4-bis-(2-pyridyl)-2-pyrroline-3-carbonitrile; m.p. 203°–204° C.;
2-(2-diethylaminoethylthio)-5-oxo-4,4-bis-(2-pyridyl)-2-pyrroline-3-carbonitrile; m.p. 135°–136° C.; 2-(2-ethylthio)-5-oxo-4,4-bis-(2-pyridyl)-2-pyrroline-3-carbonitrile; m.p. 180° C.

EXAMPLE 8

4,4-Diphenyl-2-isopropylthio-5-oxo-2-pyrroline-3-carbonitrile 1.2 g. Sodium is dissolved in 150 ml. ethanol, 15.2 g. 5-hydroxy-4,5-diphenyl-2-thioxo-3-pyrroline-3-carbonitrile are added thereto and the reaction mixture is boiled for 20 minutes. Within the course of 10 minutes, a solution of 7.0 g. isopropyl bromide in 25 ml. absolute ethanol is then added dropwise thereto, followed by heating under reflux for a further 3 hours. After cooling, the solvent is stripped off on a rotary evaporator and the residue triturated with 100 ml. water. The precipitate obtained is filtered off with suction and crystallised from ethanol. There are obtained 11.1 g. (64% of theory) 4,4-diphenyl-2-isopropylthio-5-oxo-2-pyrroline-3-carbonitrile in the form of colourless crystals; m.p. 160° C.

The 5-oxo-4,4-diphenyl-2-thioxopyrrolidine-3-carbonitrile of general formula (IV) formed as intermediate is prepared as follows:

13.8 g. 5-Hydroxy-4,5-diphenyl-2-thioxo-3-pyrroline-3-carbonitrile are boiled for 15 minutes, while stirring, in 300 ml. ethanol with 12.4 g. potassium carbonate. The initially deep yellow solution soon becomes lighter and almost colourless. After cooling, the suspension is poured, with stirring, into 1 liter of ice water and acidified carefully with dilute hydrochloric acid. The precipitate obtained is filtered off with suction and recrystallised from toluene. There are obtained 10.4 g. of yellowish crystals; m.p. 170° C. (decomp).

EXAMPLE 9

4,4-Diphenyl-2-isopropylthio-5-oxo-2-pyrroline-3-carbonitrile 1.2 g. Sodium is dissolved in 150 ml. ethanol, 15.2 g. 5-hydroxy-4,5-diphenyl-2-thioxo-3-pyrroline-3-carbonitrile are added thereto and the reaction mixture is then boiled for 20 minutes. A solution of 7.0 g. isopropyl bromide in 25 ml. absolute ethanol is then added dropwise thereto within the course of 10 minutes and refluxing continued for a further 3 hours. After cooling, the solvent is stripped off on a rotary evaporator and the residue is triturated with 100 ml. water. The precipitate is filtered off with suction and crystallised from ethanol. There are obtained 11.1 g. (64.0% of theory) of the desired product in the form of colourless crystals; m.p. 160° C.

2-Butylthio-4,4-diphenyl-5-oxo-2-pyrroline-3-carbonitrile is obtained in an analogous manner in a yield of 76% of theory.

EXAMPLE 10

4,4-Diphenyl-2-(1-methylpropylthio)-5-oxo-2-pyrroline-3-carbonitrile 0.8 g. Sodium is dissolved in 150 ml. absolute ethanol, 10.0 g. 5-hydroxy-4,5-diphenyl-2-thioxo-3-pyrroline-3-carbonitrile are added thereto and the reaction mixture is boiled for 30 minutes. The solvent is thereafter removed on a rotary evaporator and the residue is taken up in 100 ml. dimethylformamide. 5.1 g. sec.-Butyl bromide are added thereto, the reaction mixture is stirred for 24 hours at ambient temperature, a further 3.0 g. of the alkylating agent are again added thereto and stirring is continued for 24 hours. Thereafter, the solvent is distilled off under wafter pump vacuum and the residue is triturated with water. The precipitate is filtered off with suction, washed with water and crystallised from ethanol. There are obtained 7.0 g. of the desired product in the form of colourless crystals; m.p. 155°–156° C.

We claim:

1. A compound of the general formula:

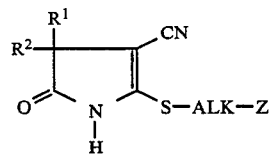

wherein $R^1$ and $R^2$ are the same or different and are phenyl, or pyridyl rings optionally substituted by up to two halogen atoms, $C_{1-4}$ alkoxy radicals, $C_{1-4}$ dialkylamino radicals or trifluoromethyl radicals, Alk is a straight-chained or branched $C_{1-4}$ alkylene chain and Z is a hydrogen atom, with the proviso that when Alk is a straight-chained alkylene chain, Z can also be an amino radical of the general formula II:

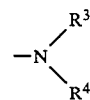

in which $R^3$ and $R^4$ are the same or different and are hydrogen atoms or methyl, ethyl, n-propyl or isopropyl radicals or, together with the nitrogen atom to which they are attached, can also form a pyrrolidino, piperidino, morpholino or piperazino radical.

2. 2-(2-Diethylaminoethylthio)-4-(4-dimethylaminophenyl)-5-oxo-4-(3-pyridyl)-2-pyrrolin-3-carbonitrile.

3. A pharmaceutical composition, comprising a compound according to claim 1, in admixture with a pharmaceutical carrier and/or adjuvant.

4. A method of treating inflammation and gastrointestinal ulcers which comprises administering orally or parenterally to a host suffering therefrom with an effective amount of a pharmaceutical composition according to claim 3.

* * * * *